United States Patent [19]

Ulmer et al.

[11] 4,237,069

[45] Dec. 2, 1980

[54] PRODUCTION OF ALPHA-HYDROXY OXIMES

[75] Inventors: Harry E. Ulmer, Chesapeake, Va.; Chempolil T. Mathew, Randolph, N.J.

[73] Assignee: Allied Chemical Corporation, Morris Township, Morris County, N.J.

[21] Appl. No.: 54,205

[22] Filed: Jul. 2, 1979

[51] Int. Cl.$^3$ .......................................... C07C 131/00
[52] U.S. Cl. .................................................... 564/258
[58] Field of Search ...................... 260/566 A, 601 H

[56] References Cited

U.S. PATENT DOCUMENTS

| | | | |
|---|---|---|---|
| 3,078,306 | 2/1963 | Schickh et al. | 260/566 A |
| 3,873,624 | 3/1975 | Mathew et al. | 260/601 R |
| 3,931,331 | 1/1976 | Mathew et al. | 260/601 R |
| 4,104,359 | 8/1978 | Davis et al. | 260/566 A |
| 4,128,580 | 12/1978 | Matsumoto et al. | 260/566 A |
| 4,155,933 | 5/1979 | Bonfield et al. | 260/566 A |

OTHER PUBLICATIONS

Ogloblin, K. A. *Chemical Abstracts*, vol. 48 (1953) #1945(g).
Kirrmann, Albert et al. Bull. Soc. Chim, France (1963) pp. 1067–1073.
Brown, John F. Jr. *J. Am. Chem. Soc.*, vol. 79 (1957) pp. 2480–2488.
Boller, D. J. et al. *J. Chem. Soc.*, (1964) pp. 2773–2776.
Roberts, John D. et al. "Basic Principles of Organic Chemistry" W. A. Benjamin, Publ. (1965) pp. 478, and 527–528.

*Primary Examiner*—Natalie Trousof
*Assistant Examiner*—L. Hendriksen
*Attorney, Agent, or Firm*—Alan M. Doernberg; Jay P. Friedenson

[57] ABSTRACT

An alpha-halo-aldehyde is reacted in aqueous media with an hydroxylamine-generating reagent at a pH between about 2 and about 9 to form the corresponding alpha-hydroxy-oxime. The products are useful as stabilizers and as complexing agents and as intermediates to unsaturated oximes, unsaturated nitriles and carbamate-type pesticides.

11 Claims, No Drawings

PRODUCTION OF ALPHA-HYDROXY OXIMES

DESCRIPTION

BACKGROUND OF THE INVENTION

The present invention relates to the production of alpha-hydroxy-oximes and particularly to the production of 2-hydroxy-2-methyl propanal oxime (also sometimes referred to as alpha-hydroxyisobutyraldehyde oxime). Alpha-hydroxyisobutyraldehyde oxime is a known compound that has been suggested by B. A. Tapper et al. in *Photochemistry*, Vol. 11, No. 3 (1972) to be an intermediate in the biosynthesis of cyanogenic glucosides. While the chloroaldehyde is well known and is relatively stable, the corresponding alpha-hydroxyaldehyde oxime is unstable and is believed to form a dimer. Chemical Abstracts, Vol. 59, No. 6387g. Alpha-hydroxyisobutyraldehyde oxime itself has been prepared in low or moderate yields by the reaction of nitrosyl sulphuric acid in liquid sulfur dioxide with isobutane, by the reaction of nitric oxide with isobutylene and by the reaction of nitrosyl chloride with isobutylene and then with a base.

BRIEF DESCRIPTION OF THE INVENTION

The present invention includes a process for producing an alpha-hydroxy-oxime which comprises reacting an alpha-halo-aldehyde of the formula:

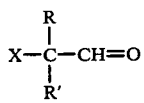

in aqueous media with an hydroxylamine-generating agent at a pH between about 2 and about 9 to form the corresponding alpha-hydroxy-oxime of the formula

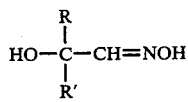

with R and R' each being independently H, alkyl, aryl, alkylaryl or any of them substituted with hydroxy, Cl or Br and X being Cl or Br.

The present invention also relates to a process for producing alpha-hydroxy-oximes which comprises reacting an aldehyde of the formula

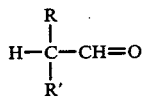

with a halogenating agent selected from Cl₂ and Br₂ and reacting the product alpha-halo-aldehyde in aqueous media with an hydroxylamine-generating reagent at a pH between about 2 and about 9 to form the corresponding alpha-hydroxy-oxime of the formula

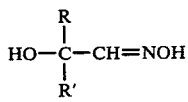

with R and R' each being independently alkyl, aryl, alkylaryl, or any of them substituted with hydroxy, Cl or Br.

DETAILED DESCRIPTION OF THE INVENTION

The present invention involves the simultaneous oximation and hydroxyl replacement of an alpha-halo-aldehyde. Alpha-halo-aldehydes such as alpha-chloro-isobutyraldehyde are known intermediates in the production of carbamate-pesticides. U.S. Pat. Nos. 3,873,624 and 3,931,331 to Mathew et al. described the chlorination of isobutyraldehyde followed by the thiomethylation of the resultant alphachloroisobutyraldehyde, followed by oximation of the thiomethylated aldehyde. The production of the chloroaldehyde is described in these patents and in other references such as C. L. Stevens et al., *J. American Chem. Soc.*, Vol. 79, 3448 (1957); A. Lorenzini et al., *J. Org. Chem.*, Vol. 32, 4008 (1967), H. Guinot et al., *Compt. Rend.*, 231 (1950) and *Chem. Abstr.*, Vol. 65, 13529h (1966).

It has been surprisingly found that oximation of haloaldehydes such as alpha-chloro-isobutyraldehyde results not merely in the replacement of the aldehyde grouping with an oxime grouping, but also in the substitution of hydroxyl for the halogen. This simultaneous reaction is especially important in the case of alpha-chloro-isobutyraldehyde and similar tertiary halo-aldehydes in that the corresponding alpha-hydroxy-aldehyde is believed not be stable, but rather to form oligomers such as dimers which would be resistant to subsequent oximation.

The conditions for the simultaneous reaction are similar to conventional conditions for the oximation of aldehydes and ketones. Thus the alpha-hydroxy-aldehyde is reacted in aqueous media with an hydroxylamine-generating reagent. As is conventional, the hydroxylamine-generating reagent may be any hydroxylamine salt, such as hydroxylamine hydrochloride, hydroxylamine sulfate, hydroxylamine phosphate, or the like. The chloride and sulfate are preferred. Active hydroxylamine reagent is generated by neutralizing such salts (which are acidic) with a base such as sodium or potassium hydroxide, ammonium hydroxide, calcium hydroxide or carbonate, or any other conventional organic or inorganic base. Because free chloride or bromide is generated in the substitution reaction, the use of hydroxylamine hydrochloride is completely compatable with the simultaneous reaction. The most preferred base for neutralization is ammonia.

The conditions of the reaction are not themselves critical. Thus the pH may be anywhere from about 2 to about 9 with more basic conditions representing merely a waste of basic reagent and more acid conditions resulting merely in a slower reaction. The preferred pH is between about 4 and about 9. The temperature of the reaction is not critical so long as all reagents, by-products and solvents remain in the liquid phase. The reaction can be conveniently conducted at or near room temperature. The concentrations of the reagents are not critical, but because of relative costs, it is preferred that the hydroxylamine-generating reagent be present in a substantially equal molar amount to the alpha-halo-aldehyde.

While the present invention is suitable for the production of alpha-hydroxy-isobutyraldehyde oxime from alpha-chloro-isobutyraldehyde, it is also suitable generally for the production of alpha-hydroxy-oximes from alpha-halo-aldehydes of the above formula where either or both of R and R' may be hydrogen such that the halogen that is being replaced may be primary or secondary. So long as one can form such a primary or secondary alpha-halo-aldehyde, the reaction of the present invention is believed capable of converting it to the corresponding alpha-hydroxy oxime. Nevertheless it is preferred that R and R' both by alkyl, aryl, alkylaryl, or any of them substituted with hydroxy, Cl or Br such that the alpha-halo substituent is on a tertiary carbon. One reason is that the halo group can be selectively produced at the alpha position by reaction of the corresponding aldehyde in which a hydrogen is attached to this tertiary carbon with $Cl_2$ or $Br_2$ in the known manner. Thus the present invention includes the preparation of such an alpha-haloaldehyde by chlorination or bromination at this site followed by simultaneous oximation and hydroxyl substitution. The conditions of the chlorination or bromination are themselves conventional and may be within the broad ranges described in U.S. Pat. Nos. 3,873,624 and 3,931,331. Alternatively the conditions described in U.S. Pat. No. 4,096,187 to Bonfield et al. (June 20, 1978) may be employed.

In using the product alpha-hydroxy-aldehyde oximes, it should be realized that on exposure to heat, many of the products and especially the ones with tertiary hydroxyls with dehydrate. Thus alpha-hydroxy-isobutyraldehyde oxime dehydrates to methacrolein oxime and then to methacrylonitrile as follows:

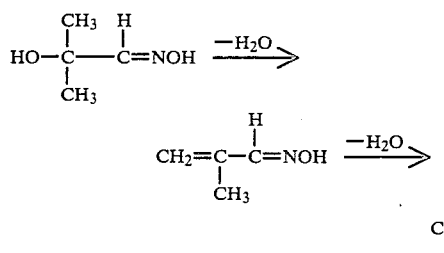

EXAMPLE 1

137 g (1.9 mol) of isobutyraldehyde was placed in a flask equipped with reflux and chlorine gas (128 g, 1.8 mol) was admitted. Alphachloroisobutyraldehyde (160 g, 1.5 mol) was distilled over at atmospheric pressure (boiling point 86°–90° C.).

In a 2 L beaker, submerged in a water-ice bath, 110 g (1.5 mol) of hydroxylamine chloride was dissolved in 800 g of water with continued mechanical stirring. The chloroaldehyde was added fresh from distillation with stirring continued from a dropping funnel over 15 minutes, and stirring was continued for 2 more hours resulting in a clear solution of pH under 0.5. With efficient cooling by the ice bath, about 240 g of 50 weight % aqueous NaOH was added. Some oily layer was then observed. The entire mass was saturated with NaCl and then extracted with ether. The extract was dried over anhydrous magnesium sulfate, the ether was removed by distillation and the oily residue vacuum distilled (boiling point about 84° C. at 3 mm mercury or about 400 Pa) to produce 139 g (1.35 mol) of 2-hydroxy-2-methyl-propanal oxime(alpha-hydroxyisobutyraldehyde oxime) for a 71% yield based on isobutyraldehyde. The product structure was confirmed by mass spectroscopy, hydrogen nuclear magnetic resonance, carbon-13 nuclear magnetic resonance, infrared spectroscopy and elemental analysis.

EXAMPLE 2

Hydroxylamine sulfate (338 g, 2.06 mol) was dissolved in 1200 mL water in a 3-liter 3-necked flask with overhead agitation and 50% NaOH solution (165 g) was added slowly with cooling to bring the pH to 6.0. Alpha-chloroisobutyraldehyde (213 g, 2.0 mols), freshly prepared as in Example 1, was then added with stirring and cooling over 15 minutes. Stirring was continued at room temperature for 2 hours more, by which time all chloroisobutyraldehyde was completed consumed (gc analysis), and the pH dropped below 0.5. More 50% NaOH solution (160 g) was added to bring pH to 6.5. The reaction mixture was saturated with NaCl and a top organic layer separated out. This was removed and the lower aqueous phase extracted with ether. The combined organic solution was dried over $MgSO_4$. Ether was removed on the rotavap, and the residue was distilled at 83°–84° C. and 3 mm mercury pressure to furnish the hydroxy oxime (168 g, 81.5%) as a colorless viscous liquid. Elemental analysis confirmed the product composition as follows:

| Found | Cal. |
|---|---|
| C = 45.41% | C = 46.60 |
| H = 8.61% | H = 8.73 |
| N = 12.02% | N = 13.59 |

EXAMPLES 3–8

Example 1 is repeated with the variations in reagents shown in Table 1.

TABLE 1

| | Aldehyde | | Halogenation | Hydroxylamine | |
|---|---|---|---|---|---|
| Example | R | R' | Agent | Salt | Base |
| 3 | ethyl | ethyl | $Cl_2$ | chloride | NaOH |
| 4 | phenyl | phenyl | $Cl_2$ | sulfate | ammonia |
| 5 | methyl | ethyl | $Cl_2$ | sulfate | ammonia |
| 6 | methyl | propyl | $Br_2$ | sulfate | KOH |
| 7 | methyl | phenyl | $Cl_2$ | sulfate | ammonia |
| 8 | methyl | t-butyl | $Br_2$ | chloride | NaOH |

In each case, the corresponding alpha-hydroxy-aldehyde oxime is produced.

EXAMPLE 9

The simultaneous oximation and hydroxyl-substitution of Example 1 is repeated by reacting 1 mol of $CH_2ClCHO$ (chloroacetaldehyde) with excess hydroxylamine chloride and sodium hydroxide. Hydroxyacetaldehyde oxime is recovered from the product by ether extraction.

EXAMPLE 10

Example 9 is repeated using one mole of $CH_3CHClCHO$ (alpha-chloro-propionaldehyde). The product $CH_3-CHOH-CH=NOH$ can be dehydrated on heating to $CH_2=CH-CH=NOH$ and then to $CH_2=CH-C\equiv N$ (acrylonitrile).

What is claimed is:
1. A process for producing an alpha-hydroxy-oxime which comprises reacting an alpha-halo-aldehyde of the formula

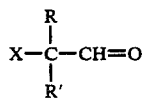

in aqueous media with an hydroxylamine-generating reagent at a pH between about 2 and about 9 to form the corresponding alpha-hydroxy-oxime of the formula

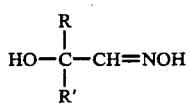

with R and R' each being independently H, alkyl, aryl, alkylaryl or any of them substituted with hydroxy, Cl or Br and X being Cl or Br.

2. The process of claim 1 wherein R and R' are each alkyl of 1–4 carbons.

3. The process of claim 1 or 2 where X is Cl.

4. The process of claim 1 where R and R' are each methyl.

5. The process of claim 1, 2 or 4 where X is Cl and the pH is between about 4 and about 9.

6. The process of claim 1, 2 or 4 wherein said hydroxylamine generating reagent is a hydroxylamine salt reacted with ammonia.

7. The process of claim 6 wherein said hydroxylamine salt is selected from the group consisting of hydroxylamine sulfate and hydroxylamine chloride.

8. A process for producing an alpha-hydroxy-oxime which comprises reacting an aldehyde of the formula

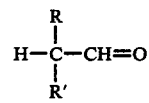

with a halogenating agent selected from the group consisting of $Cl_2$ and $Br_2$ to form the corresponding alpha-halo-aldehyde and reacting the alpha-halo-aldehyde in aqueous media with an hydroxylamine-generating reagent at a pH between about 2 and about 9 to form the corresponding alpha-hydroxy-oxime of the formula

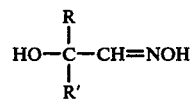

with R and R' each being independently alkyl, aryl, alkylaryl or any of them substituted with Br or Cl.

9. The process of claim 8 wherein R and R' are each alkyl of 1–4 carbons.

10. The process of claim 8 or 9 wherein said hydroxylamine generating reagent is a hydroxylamine salt reacted with ammonia.

11. The process of claim 10 wherein said hydroxylamine salt is selected from the group consisting of hydroxylamine hydrochloride and hydroxylamine sulfate.

* * * * *